(12) United States Patent
Shin et al.

(10) Patent No.: US 11,259,711 B2
(45) Date of Patent: Mar. 1, 2022

(54) DEVICE AND METHOD FOR ANALYZING CEREBROVASCULAR DISEASE AND STENOSIS BY USING PHOTOPLETHYSMOGRAPHY

(71) Applicant: Industry-Academic Cooperation Foundation, Chosun University, Gwangju (KR)

(72) Inventors: Young Suk Shin, Gwangju (KR); Hyun Goo Kang, Gwangju (KR); Seogki Lee, Gwangju (KR)

(73) Assignee: INDUSTRY-ACADEMIC COOPERATION FOUNDATION CHOSUN UNIVERSITY, Gwangju (KR)

(*) Notice: Subject to any disclaimer, the term of this patent is extended or adjusted under 35 U.S.C. 154(b) by 246 days.

(21) Appl. No.: 16/483,130

(22) PCT Filed: Apr. 28, 2017

(86) PCT No.: PCT/KR2017/004580
§ 371 (c)(1),
(2) Date: Aug. 2, 2019

(87) PCT Pub. No.: WO2018/194205
PCT Pub. Date: Oct. 25, 2018

(65) Prior Publication Data
US 2020/0229720 A1      Jul. 23, 2020

(30) Foreign Application Priority Data
Apr. 21, 2017   (KR) .................. 10-2017-0051860

(51) Int. Cl.
*A61B 5/024*      (2006.01)
*A61B 5/02*       (2006.01)
*A61B 5/00*       (2006.01)

(52) U.S. Cl.
CPC ...... *A61B 5/02427* (2013.01); *A61B 5/02007* (2013.01); *A61B 5/4064* (2013.01);
(Continued)

(58) Field of Classification Search
None
See application file for complete search history.

(56) References Cited

U.S. PATENT DOCUMENTS

2008/0275352 A1* 11/2008 Shapira ................ A61B 5/6814
600/506
2012/0136605 A1*  5/2012 Addison ................ G16H 40/40
702/98
(Continued)

FOREIGN PATENT DOCUMENTS

JP   2004-358022   12/2004
JP   2007-218780   8/2007
(Continued)

*Primary Examiner* — Yi-Shan Yang
(74) *Attorney, Agent, or Firm* — Lex IP Meister, PLLC

(57) ABSTRACT

Light is irradiated to a finger of a subject and received from the finger of the subject to extract a pulse wave signal, generates an optimized pulse wave signal in a desired type by sampling the extracted pulse wave signal according to a predetermined sampling condition and normalizes the generated pulse wave signal, the entire segment of the normalized pulse signal is divided into a plurality of window segments to detect a pulse wave amplitude value with respect to a pulse wave signal for each window, a first eigenvector for each subject corresponding to a pulse wave amplitude value of the entire window segment is extracted by using a linear discriminant analysis and then the first eigenvector per subject is compared with a threshold, determines distribution of eigenvectors for each subject compared to the threshold and thus a characteristic of the corresponding subject is diagnosed.

11 Claims, 12 Drawing Sheets

(52) U.S. Cl.
CPC .......... *A61B 5/6826* (2013.01); *A61B 5/7282* (2013.01); *A61B 5/02433* (2013.01)

(56) References Cited

U.S. PATENT DOCUMENTS

| | | | | |
|---|---|---|---|---|
| 2012/0302902 | A1* | 11/2012 | Shin | A61B 5/02225 |
| | | | | 600/494 |
| 2017/0065230 | A1* | 3/2017 | Sinha | G16H 50/20 |
| 2017/0086755 | A1* | 3/2017 | De Haan | A61B 5/02405 |
| 2021/0007607 | A1* | 1/2021 | Frank | A61B 5/02055 |

FOREIGN PATENT DOCUMENTS

| | | |
|---|---|---|
| JP | 2016-214731 | 12/2016 |
| KR | 10-2003-0061157 | 7/2003 |
| KR | 10-2012-0006440 | 1/2012 |
| KR | 10-2016-0034722 | 3/2016 |

\* cited by examiner

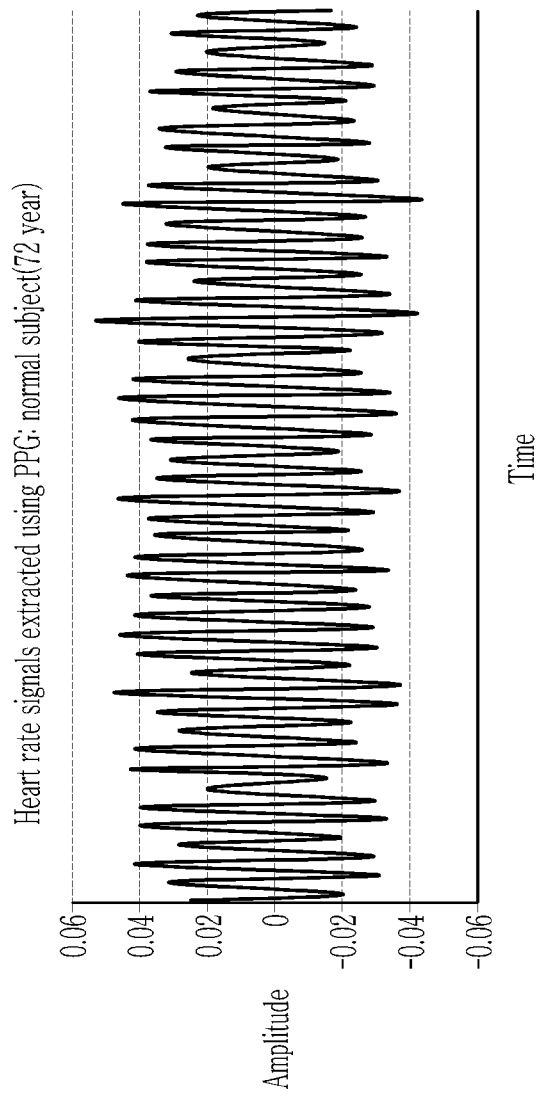

DEVICE AND METHOD FOR ANALYZING CEREBROVASCULAR DISEASE AND STENOSIS BY USING PHOTOPLETHYSMOGRAPHY

TECHNICAL FIELD

The present invention relates to a device for analyzing a cerebrovascular disease and stenosis using photoplethysmography (PPG), and a method thereof.

BACKGROUND ART

Currently, cerebral artery stenosis is diagnosed by using a transcranial doppler test, computer tomography (CT), or magnetic resonance imaging (MRI), and carotid stenosis is diagnosed by carotid angiography using carotid ultrasound or MRI to determine the severity of the carotid artery stenosis.

However, in the case of angiographic CT, it is an invasive test that has the burden of exposing radiation, and both CT and MRI can cause side effects due to the contrast agent.

DISCLOSURE

Technical Problem

The present invention has been made in an effort to provide a device for analyzing a cerebrovascular disease and stenosis using photoplethysmography, which can determine the severity of stenosis of a cerebral artery connected to a cerebrum from a neck, and a method thereof.

The present invention provides a device for analyzing a cerebrovascular disease and stenosis using photoplethysmography, which allows simple identification of a normal person and a cerebral artery stenosis patient using a non-invasive and simple measurement of periodic characteristic and waveform pattern analysis of PPG signals, and a method thereof.

In addition, the present invention aims to solve the problems of the cerebral artery disease and stenosis using a device using photoplethysmography, which enables measurement at a low cost and analysis of the severity of cerebral artery stenosis of a subject with a short measurement time of 60 to 120 seconds, and a method thereof.

In addition to the above-mentioned objectives, the exemplary embodiment of the present invention may be used for other objectives that are not mentioned in detail herein.

Technical Solution

In order to solve the above-stated problems, according to exemplary embodiments of the present invention, a device for analyzing a cerebrovascular disease and stenosis using photoplethysmography (PPG) is provided. The device includes: a PPG probe where a finger of a subject is seated, and irradiating light to and receiving light from the finger of the subject; a pulse wave signal extracting portion that extracts a pulse wave signal from an optical signal received from the PPG probe; a sampling portion that carries out sampling on the pulse wave signal according to a predetermined sampling condition and generates an optimized pulse wave signal of a desired type; a pulse wave signal normalization portion that generates a normalized pulse wave signal with pulse wave signals of the subject, that is optimized by the sampling portion; a pulse wave amplitude detection portion that divides the whole segments of the normalized pulse wave signal into a plurality of window segments, and detects a pulse wave amplitude value with respect to a pulse wave signal for each window; a cerebral artery stenosis characteristic analyzing portion that extracts a first eigenvector for each subject, corresponding to a pulse wave amplitude value of the entire window segments by applying linear discriminant analysis to the pulse wave amplitude value per window, detected by the pulse wave amplitude detection portion; and a cerebral artery stenosis diagnosis portion that compares the first eigenvector per subject with a threshold to diagnose a characteristic of the subject.

The cerebral artery stenosis characteristic analyzing portion calculates eigenvalues for corresponding amplitude values of the entire window segments per subject by applying a pulse wave amplitude value per window, detected by the pulse wave amplitude detection portion, to a linear discriminant analysis algorithm, and determines an eigenvector having the highest eigenvalue among the calculated eigenvalues as a first eigenvector.

The cerebral artery stenosis characteristic analyzing portion diagnoses the corresponding subject as a patient when the first eigenvector is greater than the threshold.

The device for analyzing a cerebrovascular disease and stenosis using PPG according to the exemplary embodiment of the present invention further includes a pulse wave notch detection portion that divides the whole segments of a normalized pulse wave signal of a subject into a plurality of window segments, detects a notch position in a pulse wave signal for each window, and provides notch position information, wherein the cerebral artery stenosis diagnosis portion diagnoses a characteristic of the subject by using the notch position information.

The device for analyzing a cerebrovascular disease and stenosis using PPG according to the exemplary embodiment of the present invention further includes a wax/wane wave detection portion that divides the whole segment of the normalized pulse wave signal of the subject into a plurality of window segments, and detects a wax/wane waveform from a pulse wave signal of each window, wherein the cerebral artery stenosis diagnosis portion diagnoses a characteristic of the subject by using the wax/wane waveform.

The pulse wave amplitude detection portion detects a maximum amplitude value with respect to a pulse wave signal for each window.

According to an exemplary embodiment of the present invention for solving the above-stated problems, a method for analyzing a cerebrovascular disease and stenosis using photoplethysmography (PPG) is provided. The method includes: irradiating light to a finger of a subject and receiving light; extracting a pulse wave signal from the received optical signal; generating an optimized pulse wave signal of a desired type by carrying out sampling on the pulse wave signal according to a predetermined sampling condition; generating a normalized pulse wave signal with the optimized pulse wave signals; dividing the entire segment of the normalized pulse wave signal into a plurality of window segments and detecting a pulse wave amplitude value with respect to a pulse wave signal for each window; extracting a first eigenvector for each subject, corresponding to a pulse wave amplitude value of the entire window segments by applying linear discriminant analysis to the pulse wave amplitude value per window, detected by a pulse wave amplitude detection portion; and diagnosing a characteristic of a subject by comparing a first eigenvector for each subject with a threshold.

The first eigenvector corresponds to a eigenvalue having the highest value among eigenvalues calculated by applying a pulse wave amplitude value per window, detected by the pulse wave amplitude detection portion, to a linear discriminant analysis algorithm.

In the diagnosing the characteristic of the subject, the subject is diagnosed as a patient when the first eigenvector is greater than the threshold.

The method for analyzing a cerebrovascular disease and stenosis using PPG according to the exemplary embodiment of the present invention further includes: dividing the entire segment of a normalized pulse wave signal of a subject into a plurality of window segments, and detecting a notch position in a pulse wave signal for each window; and diagnosing a characteristic of a subject by using a notch position for each window.

The method for analyzing a cerebrovascular disease and stenosis using PPG according to the exemplary embodiment of the present invention further includes: dividing the entire segment of a normalized pulse wave signal of a subject into a plurality of window segments, and detecting a wax/wane waveform from a pulse wave signal for each window; and diagnosing a characteristic of a subject by using the wax/wane waveform.

In the extracting the pulse wave signal, a pulse wave signal of a right hand finger or a left hand finger, or the right hand finger and the left hand finger of the subject, are extracted.

Advantageous Effects

According to an exemplary embodiment of the present invention, a non-invasive method of detecting a pulse wave signal from a subject's finger allows a simple identification of normal persons and patients with cerebral artery stenosis.

In addition, according to an exemplary embodiment of the present invention, early diagnosis of asymptomatic patients with cerebral artery stenosis can prevent the threat of cerebral infarction.

Further, according to an exemplary embodiment of the present invention, it is possible to pre-analyze the severity of cerebral artery stenosis in a short time at a low cost.

DESCRIPTION OF THE DRAWINGS

FIG. 9A and FIG. 9B show wax/wane waveforms of a normal person and a patient according to the exemplary embodiment of the present invention.

MODE FOR INVENTION

Figure 1:
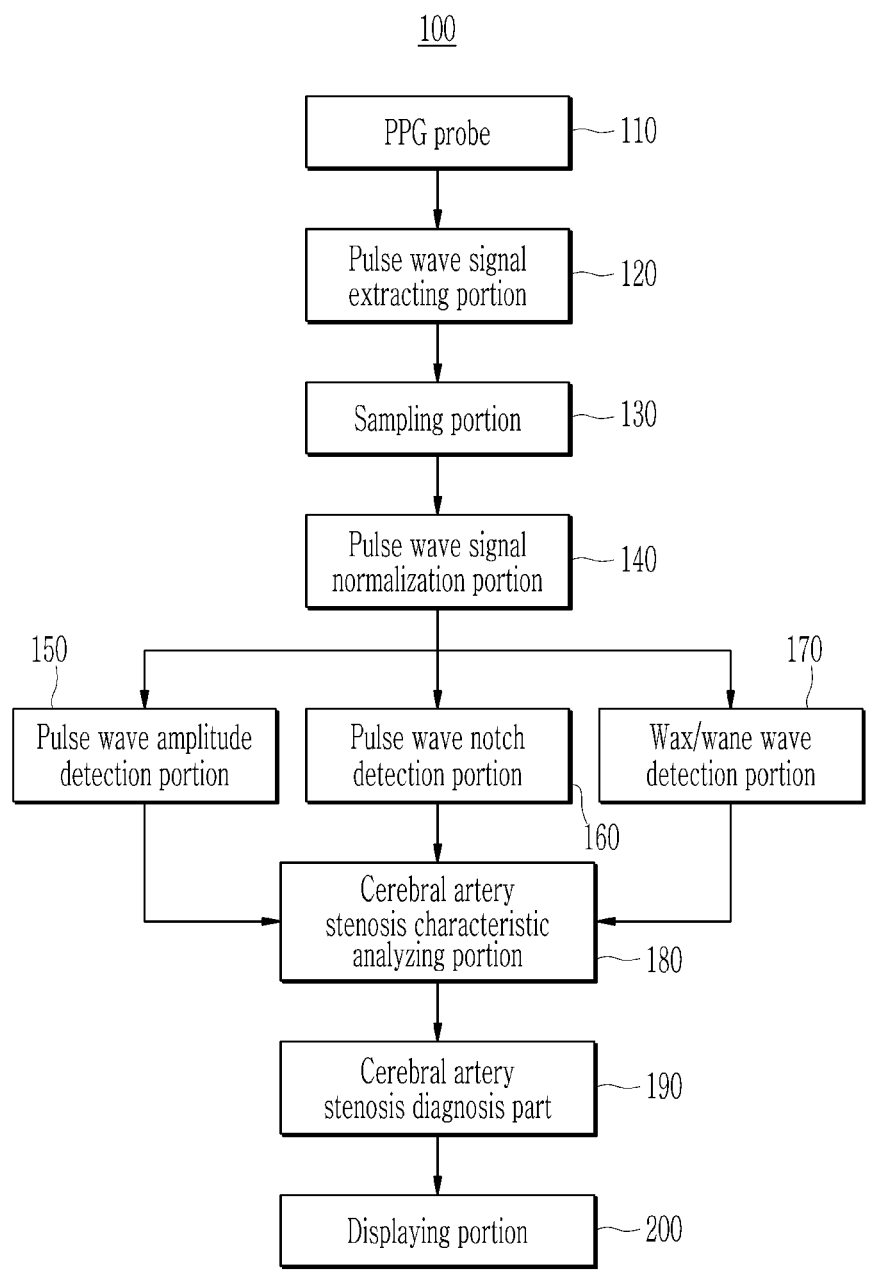
FIG. 1 is a block diagram of a device for analyzing a cerebrovascular disease and stenosis using photoplethysmography.

In the following detailed description, only certain exemplary embodiments of the present invention have been shown and described, simply by way of illustration. As those skilled in the art would realize, the described embodiments may be modified in various different ways, all without departing from the spirit or scope of the present invention. Accordingly, the drawings and description are to be regarded as illustrative in nature and not restrictive. Like reference numerals designate like elements throughout the specification.

In addition, well known technologies will not be described in detail.

Unless explicitly described to the contrary, the word "comprise" and variations such as "comprises" or "comprising" will be understood to imply the inclusion of stated elements but not the exclusion of any other elements. Further, terms including "unit", "module", and the like disclosed in the specification mean a unit that processes at least one function or operation, and may be implemented by hardware, software, or a combination of hardware and software.

Hereinafter, a device for analyzing a cerebrovascular disease and stenosis using photoplethysmography, and a method thereof according to an exemplary embodiment of the present invention, will be described with reference to the accompanying drawings.

Prior to the description, photoplethysmography is a pulse waveform obtained by measuring a volume change due to a pressure change of elastic blood vessels using optical signals such as infrared rays, visible rays, or a laser.

FIG. 1 is a block diagram of a device for analyzing a cerebrovascular disease and stenosis using photoplethysmography. Referring to FIG. 1, a device for analyzing a cerebrovascular disease and stenosis using photoplethysmography (hereinafter referred to as an analysis device) 100 according to an exemplary embodiment of the present invention includes a PPG probe 110, a pulse wave signal extracting portion 120, a sampling portion 130, a pulse wave signal normalization portion 140, a pulse wave amplitude detection portion 150, a pulse wave notch detection portion 160, a wax/wane wave detection portion 170, a cerebral artery stenosis characteristic analyzing portion 180, a cerebral artery stenosis diagnosis portion 190, and a display portion 200. Meanwhile, the analysis device 100 may exclude the pulse wave notch detection portion 160 and the wax/wane wave detection portion 170, or may use only one of the pulse wave notch detection portion 160 and the wax/wane wave detection portion 170 depending on the case.

The analysis device 100 according to the exemplary embodiment of the present invention may be implemented as a single device, or may be implemented as a manometer including a computer and a monitor that includes the PPG probe 110 and the pulse wave signal extracting portion 120, and a computer/monitor including the sampling portion 130, the pulse wave signal normalization portion 140, the pulse wave amplitude detection portion 150, the pulse wave notch detection portion 160, the wax/wane wave detection portion 170, the cerebral artery stenosis characteristic analyzing portion 180, the cerebral artery stenosis diagnosis portion 190, and the display portion 200.

The PPG probe 110 is a constituent element where a finger of a subject is led in or placed, and irradiates an optical signal such as an infrared ray, a visible ray, or a laser to a region to be examined, and receives transmitted light that is not absorbed into tissue but transmitted or reflected light reflected from the tissue. For such a function, the PPG probe 110 includes a light emission portion (not shown) that irradiates light and a light receiving portion (not shown) that receives light, and as such a configuration and operation of the PPG 110 are known art, no further detailed description will be provided.

Figure 2:
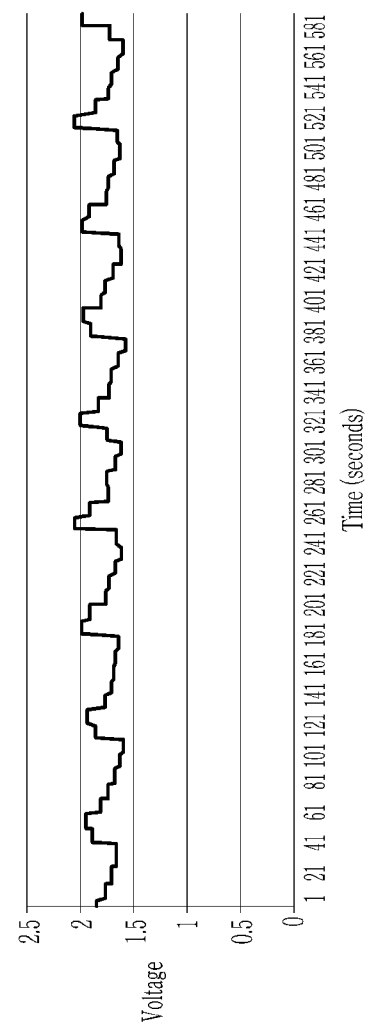
FIG. 2 is an example of an original PPG pulse wave signal acquired by the device for analyzing the cerebrovascular disease and stenosis using photoplethysmography according to the exemplary embodiment of the present invention.

The pulse wave signal extracting portion 120 amplifies and filters the amount of light or brightness degree data, extracts a pulse wave signal of a using by using a filtered data signal, and stores the extracted pulse wave signal in a storage unit (not shown). An example of a pulse wave signal extracted by the pulse wave signal extracting portion 120 is illustrated in FIG. 2. FIG. 2 is an example of an original PPG pulse wave signal acquired by the device for analyzing the cerebrovascular disease and stenosis using photoplethysmography according to the exemplary embodiment of the present invention. In FIG. 2, the vertical axis denotes a voltage value and the horizontal axis denotes time.

The sampling portion 130 samples a pulse wave signal of the subject extracted by the pulse wave signal extracting portion 120 according to a predetermined sampling condition to generate a desired type of pulse wave signal.

Figure 3:
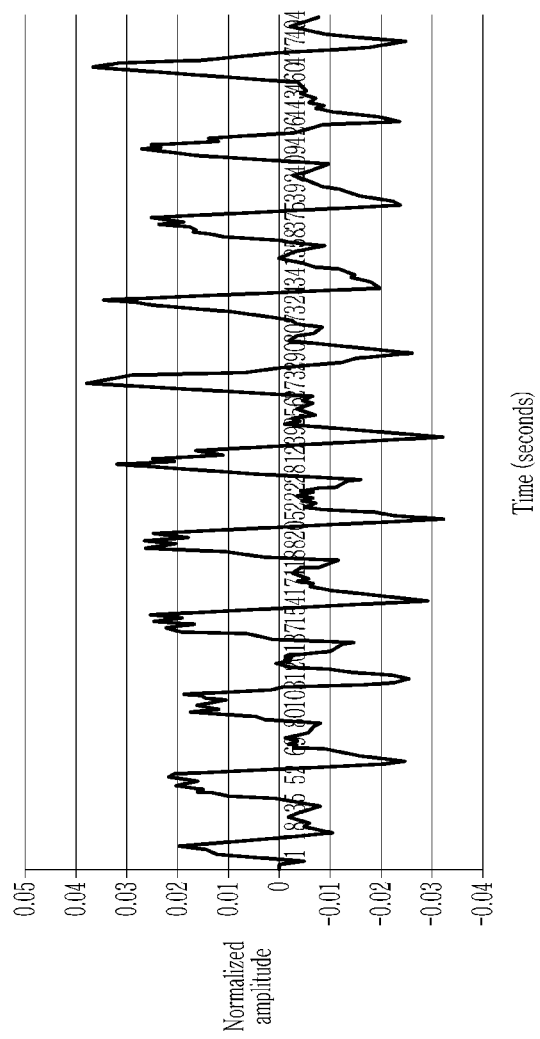
FIG. 3 shows an example of a pulse wave signal resampled by a sampling portion according to the exemplary embodiment of the present invention.

In detail, the sampling portion 130 performs resampling to acquire a predetermined amount of data for a predetermined time period from the original pulse wave signal of the subject. An example of the resampling is shown in FIG. 3. As an example of a pulse wave signal resampled by the normalization portion according to the exemplary embodiment of the present invention, FIG. 3 shows a result of resampling carried out to extract 66,000 pieces of data during one minute (60 seconds).

Figure 4:
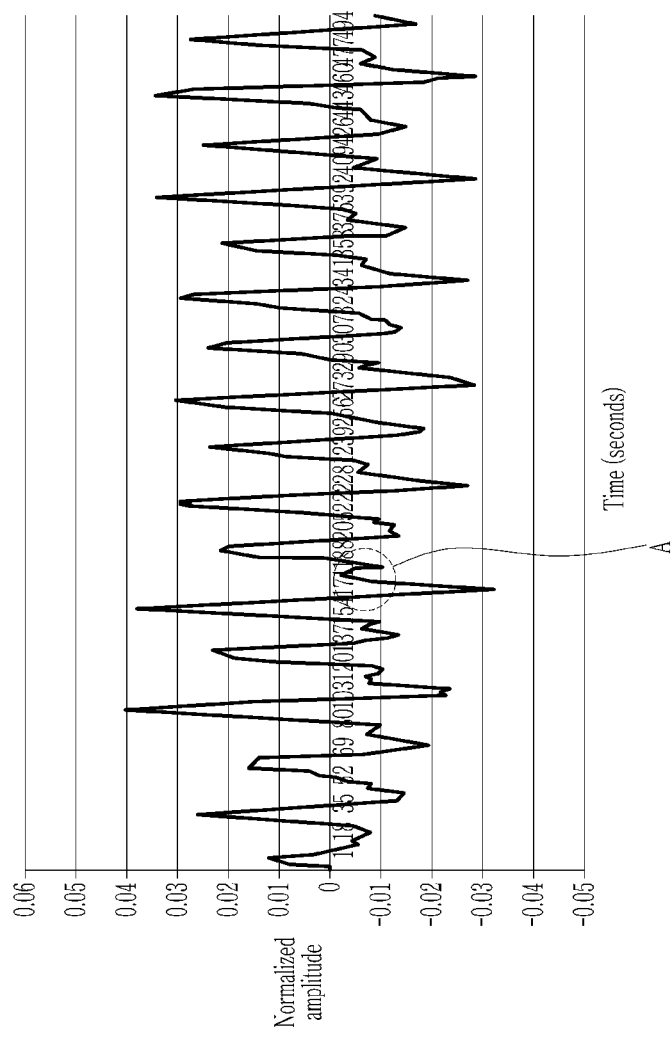
FIG. 4 shows an example of a pulse wave signal finally processed by the sampling portion according to the exemplary embodiment of the present invention.

When the original pulse wave signal is resampled, the sampling portion 130 smoothens the resampled pulse wave signal to generate an optimally sampled pulse wave signal as shown in FIG. 4.

For example, the sampling portion 130 can generate an optimized sampled pulse wave signal by setting the sampling interval to 23 segments for 66,000 pieces of data.

In this case, it is preferable to adjust the sampling intervals to reveal a pulse wave notch (refer to A in FIG. 4) in the optimally sampled pulse wave signal during the optimal sampling, and it is preferable that a pulse wave extracted from one sampling interval (i.e., one segment from 23 segments) includes an average heart rate per minute. For example, when 66,000 pieces of data are divided into 23 segments for resampling of the data, about 2869 pieces of data may be included in each segment and about 60 to 80 pulse waves exist in 2869 pieces of data.

The resampling and optimal sampling are applied equally to all original pulse wave signals obtained by measuring the same subject multiple times.

The pulse wave signal normalization portion 140 normalizes a plurality of pulse wave signals of each subject, that are optimally sampled by the sampling portion 130, and outputs normalized pulse wave signals to reduce a change of the pulse wave signals that are changed per measurement time of the same subject. In this case, the pulse wave signal normalization portion 140 normalizes a pulse wave signal corresponding to a subject based on Equation 1.

Herein, a total number of measurements (e.g., when the number of measurements per person is 5 and the number of subjects is 10, the total number of measurements becomes 50) is W and the number of subjects is N.

$$W=\{W_i\}_{i=1}^N$$

In addition, a pulse wave signal acquired from the same subject may be represented as $W_i=\{W_{ij}\}_{j=1}^{N_i}$, and a pulse wave signal ($W_{ij}$) denotes a j-th pulse wave signal of an i-th subject.

$$\varphi=\text{sqrt}(\Sigma_{j=1}^{N_i}(w_{ij})^2)$$

$$W^*_i=W_i/\varphi \qquad \text{[Equation 1]}$$

In Equation 1, a pulse wave size value $\varphi$ of the same subject is a value obtained by squaring pulse wave signals of the same subject and adding the same. In addition, a normalized pulse wave signal $W^*_i$ is normalized pulse wave signals, which are obtained by dividing pulse signal waves of the subject by the pulse wave size value $\varphi$.

The pulse wave amplitude detection portion 150 divides the whole segments of the normalized pulse wave signals of each subject into a plurality of window segments, detects a pulse wave amplitude value with respect to a pulse wave signal per window, and provides the detected pulse wave amplitude value to the cerebral artery stenosis characteristic analyzing portion 180.

The pulse wave notch detection portion 160 divides the whole segments of a normalized pulse wave signal of each subject into a plurality of window segments, detects a notch position in a pulse wave signal per window, determines information on the notch position, and provides the determined information to the cerebral artery stenosis characteristic analyzing portion 180. In this case, information on the notch position, that is, the notch position information, includes information on whether or not a notch exists, and a voltage value at the corresponding notch position if a notch exists.

The wax/wane wave detection portion 170 divides the whole segment of a normalized pulse wave signal of each subject into a plurality of window segments, detects a wax/wane pattern from a pulse wave signal of each window, and provides the detected wax/wane pattern to the cerebral artery stenosis characteristic analyzing portion 180.

The the number of window segments and the number of windows are equal to each other in each of the pulse wave amplitude detection portion 150, the pulse wave notch detection portion 160, and the wax/wane wave detection portion 170, and operation for dividing the entire segment of a normalized pulse wave signal of each subject into a plurality of window segments is carried out in one (one of 150 to 170) of the constituent elements, and then a pulse wave signal for each window can be shared with other constituent elements.

The cerebral artery stenosis characteristic analyzing portion 180 applies an amplitude value of each pulse wave per window received from the pulse wave amplitude detection portion 150 to a linear discriminant analysis (LDA) algorithm to extract a first eigenvector that corresponds to the pulse wave amplitude value extracted from the entire window segment, and provides the extracted first eigenvector of the subject to the cerebral artery stenosis diagnosis part 190.

Here, the LDA algorithm reflects the global characteristic of the individually extracted entire window values rather than reflecting the local characteristic of each window. For example, after extracting 60 features by (60 window values/1 person), the LDA algorithm extracts 60 major eigenvectors, the highest explanatory eigenvector of 60 overall features becomes the first eigenvector, the next explanatory eigenvector becomes a second eigenvector, and the sixtieth eigenvector is the least explanatory. The criterion for finding the highest explanatory eigenvector is determined by eigenvalues, and the eigenvector corresponding to the largest eigenvalue is called the first eigenvector.

The cerebral artery stenosis characteristic analyzing portion 180 analyzes the notch position information of each window received from the pulse wave notch detection portion 160, and determines whether the notch position information exists and the number of windows in which the notch position has a voltage value of 0 V or more if the notch position information exists.

The cerebral artery stenosis characteristic analyzing portion 180 receives the window wax/wane pattern from the wax/wane wave detection portion 170, and analyzes the wax/wane pattern of each window to extract the characteristics of the wax/wane pattern. At this time, the feature of the wax/wane pattern extracts waveform change, that is, amplitude change and interval change.

The cerebral artery stenosis diagnosis portion 190 diagnoses the subject's large cerebral artery stenosis through the first eigenvector extracted from the entire window segment received from the pulse wave amplitude detection portion 150. The pulse amplitude values extracted from the entire window segment have one first eigenvector for each subject. For example, the cerebral artery stenosis diagnosis portion 190 compares the first eigenvector of the subject with a threshold, determines that the corresponding subject is a patient when the first eigenvector is larger than the threshold, and determines that the corresponding subject is a normal person when the first eigenvector is less than the threshold. In addition, the cerebral artery stenosis diagnosis portion 190 determines a difference between the first eigenvector and the threshold for each subject, and diagnoses the degree of the symptom using the difference value by the subject.

For reference, the first eigenvector of a subject's pulse wave signal is generally larger than "0" in a window-based pulse wave signal for an actual patient, and in the case of a normal person, the first eigenvector of the subject is generally smaller than "0". In patients with severe symptoms, the first eigenvector is greater than "0", and the first eigenvector is closer to "0" in patients with lesser symptoms.

On the other hand, it is possible to determine whether the subject is a normal person or a patient by determining information on the position of the pulse wave notch in the window pulse wave signal. The position of the pulse wave notch in the window pulse wave signal for the actual patient appears at a position higher than "0" or does not show a pulse wave notch, and in the case of a normal person, the pulse wave notch position appears at a position lower than "0". Thus, the cerebral artery stenosis diagnosis portion 190 receives and analyzes the position of the pulse wave notch of the window to diagnose whether the subject is a normal person or a patient.

It is also possible to determine whether the subject is a normal person or a patient by determining the information about the wax/wane pattern in the window pulse wave signal. In the case of normal subjects, the wax/wane pattern is evenly distributed throughout the waveform. That is, the maximum amplitude value and the minimum amplitude value of the wax/wane waveform do not vary with time, and the change in the interval between neighboring waveforms is not large. On the other hand, in case of an actual patient, the maximum amplitude value and the minimum amplitude value of the wax/wane waveform fluctuate with time and the interval between neighboring waveforms changes greatly. As the symptoms are more severe, the variation of the maximum amplitude and the minimum amplitude of the wax/wane waveform becomes greater over time and the variation of the interval between neighboring waveforms becomes greater. Accordingly, the cerebral artery stenosis diagnosis portion 190 receives and analyzes the wax/wane pattern per window to diagnose whether the subject is a normal person or a patient.

The cerebral artery stenosis diagnosis portion 190 can diagnose whether the subject has cerebral artery stenosis and the degree of the cerebral artery stenosis by only using the first eigenvector, but for more precise analysis, the cerebral artery stenosis diagnosis portion 190 may use a signal output from at least one of the pulse wave notch detection portion 160 and the wax/wane wave detection portion 170.

The displaying portion 200 displays the first eigenvector of each subject detected by the pulse wave amplitude detection portion 150 on the screen based on the threshold, or displays the pulse wave notch position detected by the pulse wave notch detection portion 160 with reference to a pulse wave signal or the wax/wane waveform acquired from the wax/wane wave detection portion 170 on the screen. When the outputs of the pulse wave amplitude detection portion 150, the pulse wave notch detection portion 160, and the wax/wane wave detection portion 170 are displayed on the screen, a diagnostician directly views the information displayed on the screen without using the cerebral artery stenosis diagnosis portion 190 to determine whether the subject is a normal person or a patient, or how serious the symptoms are.

In addition, the displaying portion 200 displays information detected or determined in the cerebral artery stenosis diagnosis portion 190 on the screen.

Figure 5:
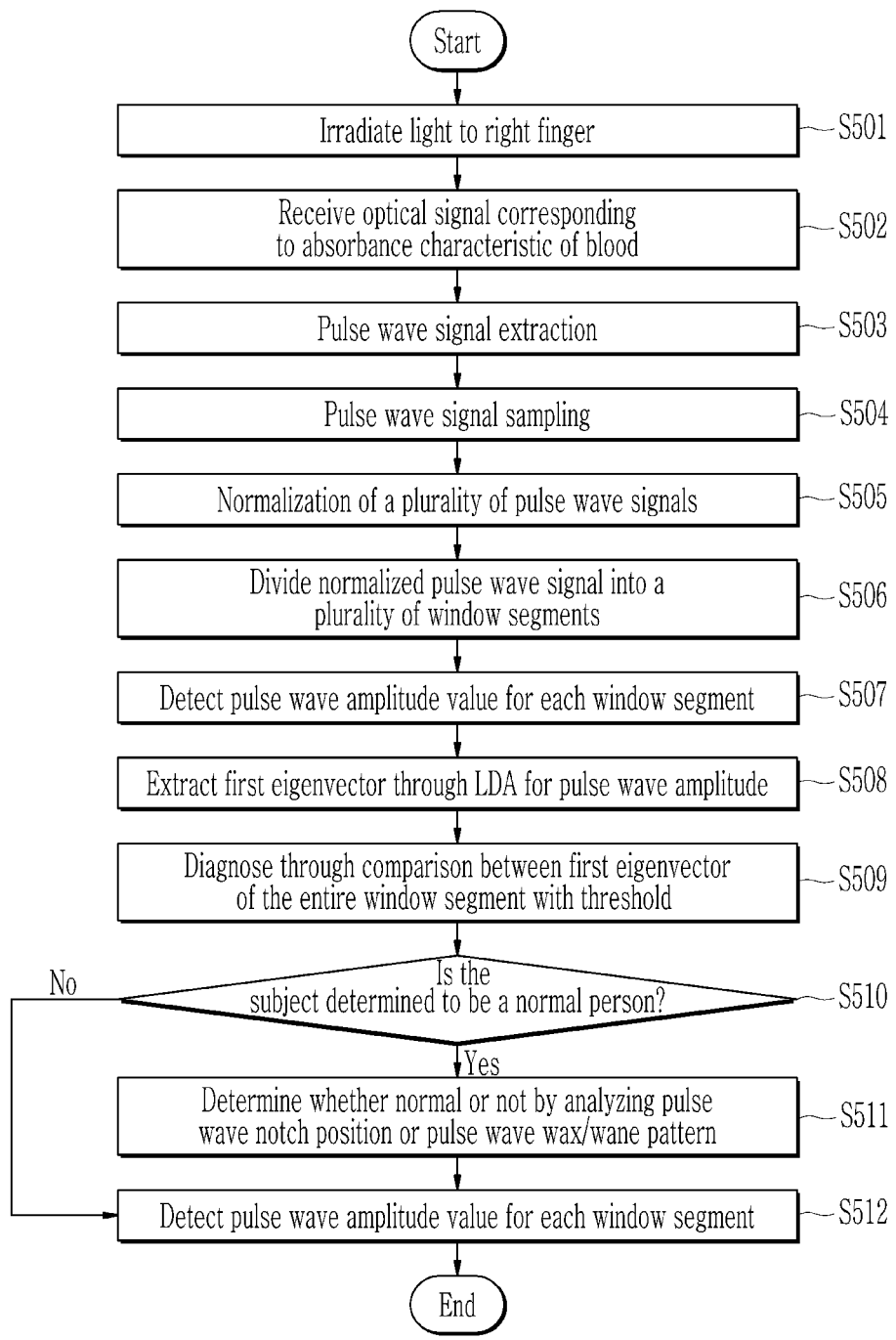
FIG. 5 is a flowchart of a method for analyzing a cerebrovascular disease and stenosis using photoplethysmography according to an exemplary embodiment of the present invention.

Hereinafter, a method for analyzing a cerebrovascular disease and stenosis using photoplethysmography will be described with reference to FIG. 5.

The subject starts the diagnosis by placing a finger of one hand or fingers of both hands on the PPG probe 110. The symptoms of cerebral artery stenosis affect the pulse wave signal of the right fingers more than the left fingers. Using the pulse wave signal of the fingers of two hands is more accurate than using the pulse wave signal of one finger, but a sufficient result can be obtained by using the pulse wave signal of the finger of one hand.

In the following description, the using of the right finger will be described as an example.

When the subject is seated and the right finger is placed on the PPG probe 110, the PPG probe 110 irradiates light for a predetermined measurement time set by the PPG probe 110 (S501), and receives the irradiated light which has been transmitted through or reflected from the right finger (S502). The predetermined measurement time is, for example, 60 to 120 seconds. The same subject repeats the measurement so that steps S501 and S502 are repeated a plurality of times.

At each measurement, the optical signal received by the PPG probe 110 is input to the pulse wave signal extracting portion 120, and the pulse wave signal extracting portion 120 extracts the pulse wave signal from the optical signal and stores the extracted pulse wave signal to the storage unit (not shown) (S503).

When the measurement of the same subject is performed a plurality of times, the sampling portion 130 reads the pulse wave signal for the same subject in the storage unit and resamples the read pulse wave signal to extract 66,000 pieces of data in one minute (60 seconds) so as to extract 66,000 pieces of data, and generates an optimally sampled pulse wave signal by optimally sampling the resampled 66,000 pieces of data into 23 segment units (S504).

The pulse wave signal normalization portion 140 normalizes the subject's optimally sampled pulse wave signals using Equation 1 to reduce the variation of pulse wave signals that change for each measurement of the same subject, and outputs the normalized pulse wave signal of the subject to the pulse wave amplitude detection portion 150, the pulse wave notch detection portion 160, and the wax/wane wave detection portion 170 (S505).

The pulse wave amplitude detection portion 150 divides the pulse wave signal that is normalized by the pulse wave signal normalization portion 140 into a plurality of window segments (S506), and detects a pulse wave amplitude value per each window segment, and provides the detected value to the cerebral artery stenosis characteristic analyzing portion 180 (S507).

For example, the pulse wave amplitude detection portion 150 may detect and provide one of a maximum amplitude pulse (MXAP) and a minimum amplitude pulse (MIAP) or may detect and provide both of the maximum amplitude pulse and the minimum amplitude pulse. In dividing the normalized pulse wave signal into a plurality of window segments, it is preferable that the number of windows is obtained based on the pulse vibration waveform number including at least one heartbeat.

Figure 6:
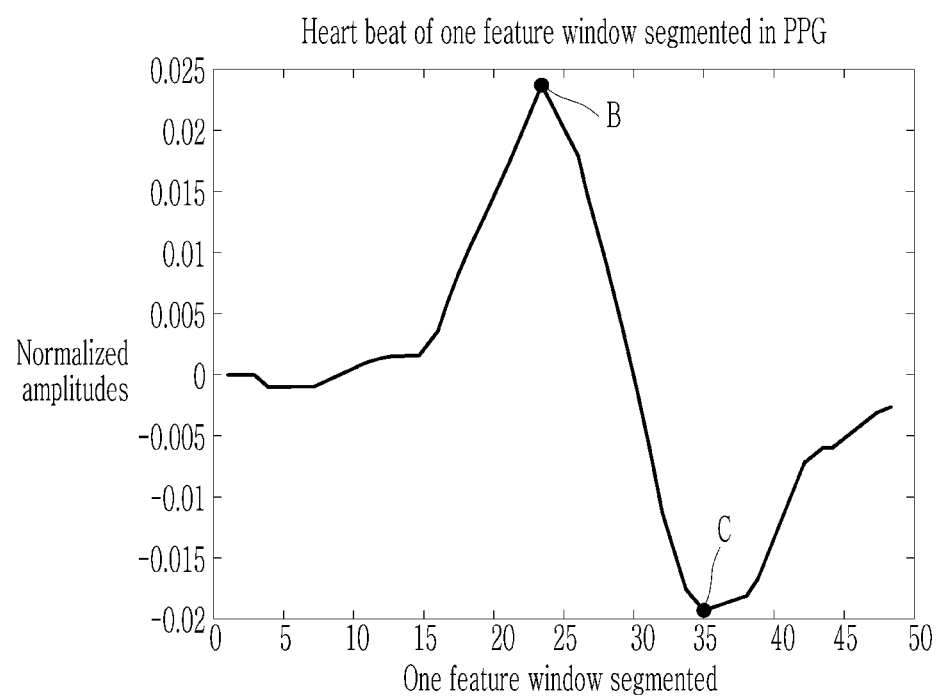
FIG. 6 shows a maximum amplitude pulse and a minimum amplitude pulse in the pulse wave signal according to the exemplary embodiment of the present invention.

The MXAP and the MIAP detected by the pulse wave amplitude detection portion 150 are exemplarily shown in FIG. 6. FIG. 6 shows a maximum amplitude pulse and a minimum amplitude pulse in the pulse wave signal according to the exemplary embodiment of the present invention. Referring to FIG. 6, a maximum amplitude pulse B and a minimum amplitude pulse C are detected in one feature window segment among 60 feature windows divided from a normalized pulse wave signal.

The cerebral artery stenosis characteristic analyzing portion 180 applies an LDA algorithm to the maximum amplitude pulse or the minimum amplitude pulse or the maximum and minimum amplitude values per window, received from the pulse wave amplitude detection portion 150, to calculate eigenvalues with respect to amplitude values corresponding to the entire window segments, and determines an eigenvalue corresponding to the highest eigenvalue among calculated eigenvalues as a first eigenvector of each subject and provides the determined first eigenvector per subject to the cerebral artery stenosis diagnosis portion 190 (S508).

Then, the cerebral artery stenosis diagnosis portion 190 identifies (i.e., diagnoses) a normal person or a patient based on a threshold with the first eigenvector with respect to a pulse wave signal per subject (S509). For example, when the threshold is "0", the cerebral artery stenosis diagnosis portion 190 compares the first eigenvector of the subject to the threshold "0" to determine a subject of which the first eigenvector is more than zero and a subject of which the first eigenvector is less than zero. The cerebral artery stenosis diagnosis portion 190 calculates a difference between the first eigenvector and the value of 0 for each subject.

The cerebral artery stenosis diagnosis portion 190 diagnoses a subject with a first eigenvector of greater than or equal to zero as a patient, and a subject with a first eigenvector of less than zero as a normal person. The diagnosis method in the cerebral artery stenosis diagnosis portion 190 is not limited to the above-described method and can be achieved in various other ways.

Figure 7A:
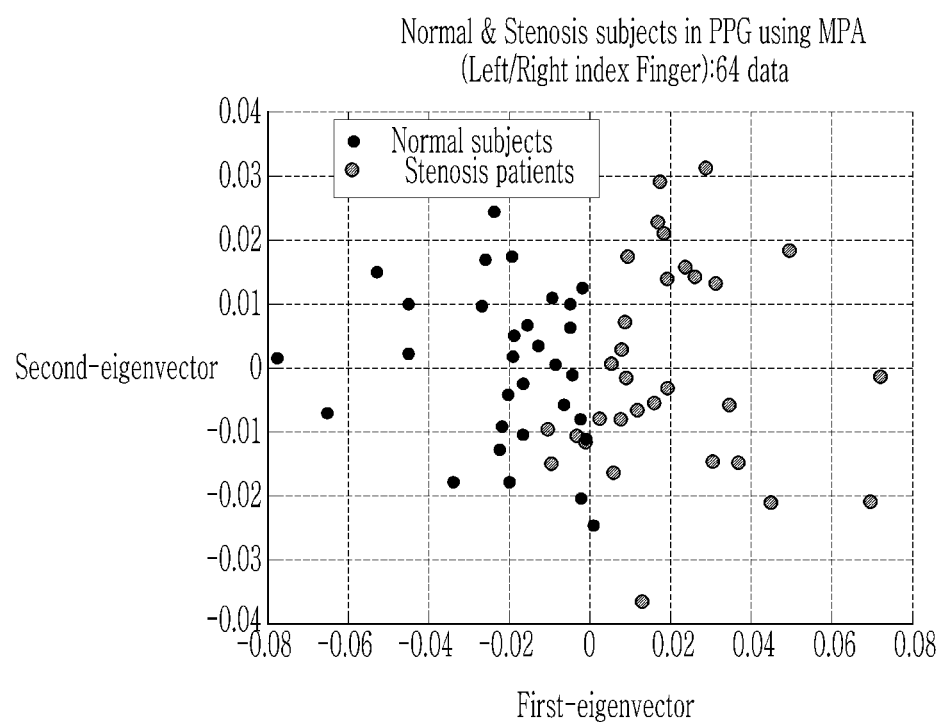
FIG. 7A and FIG. 7B show distribution of a first eigenvector and a second eigenvector corresponding to the amplitude of the pulse wave signal according to the exemplary embodiment of the present invention.
Figure 7B:
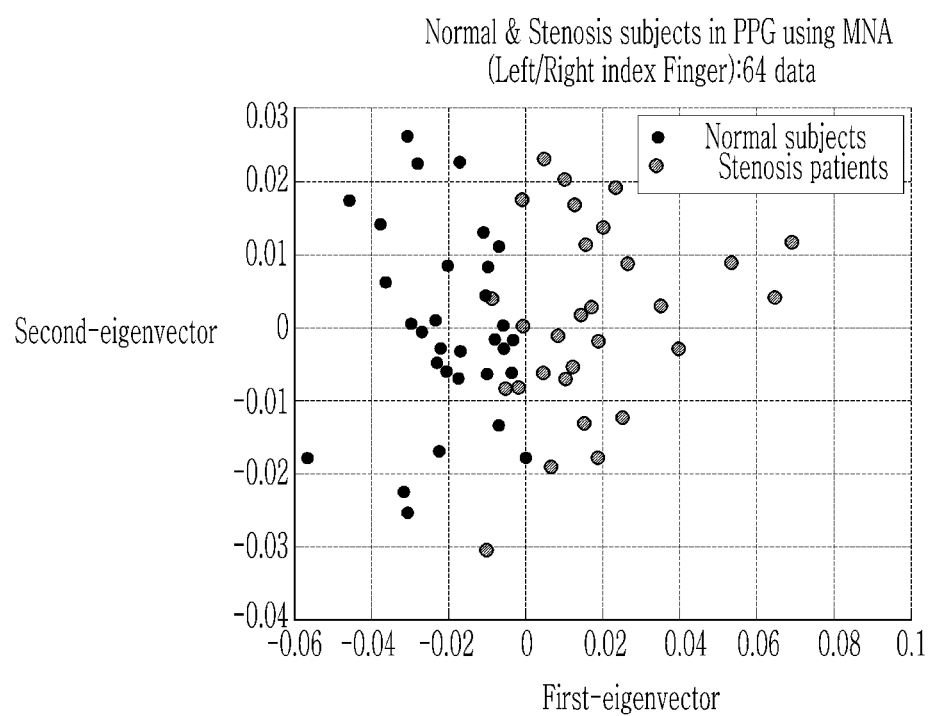

The above-described diagnosis in the cerebral artery stenosis diagnosis portion 190 will be described with reference to FIG. 7A and FIG. 7B. FIG. 7A and FIG. 7B show distribution of a first eigenvector and a second eigenvector corresponding to the amplitude of the pulse wave signal according to the exemplary embodiment of the present invention, and the distribution shown in 7A and FIG. 7B can be displayed on the screen through the displaying portion 200.

Referring to FIG. 7A and FIG. 7B, the distribution chart with respect to the first eigenvector per subject is a result of dividing a pulse wave signal extracted after optimal sampling of pulse wave signals from the right hand index finger and the left hand index finger into 60 feature window segments, and classifying normal persons and cerebral artery stenosis patients by applying a linear discrimination analysis algorithm using a maximum amplitude value and a minimum amplitude value detected from each feature window segment. Here, a total of 64 subjects were targeted, and 32 among the 64 were normal persons (average age: 59.8, standard deviation: 14.6), and 32 were patients (average age: 62.7, standard deviation: 11.2).

FIG. 7A is a distribution chart of first and second eigenvectors corresponding to a maximum positive amplitude (MPA) per subject, and FIG. 7B is a distribution chart of first and second eigenvectors corresponding to the maximum negative amplitude (MNA) per subject. In FIG. 7A and FIG. 7B, the horizontal axis indicates a value of a first eigenvector and the vertical axis indicates a value of a second eigenvector, which is the second highest value. Substantially, distribution with respect to the first eigenvector may not be indicated in conjunction with the second eigenvector, and may be replaced by an eigenvector other than the second eigenvector.

The black dot two-dimensionally represents first and second eigenvectors per subject for normal persons, and the gray dot two-dimensionally represents a two-dimensional image composed of the first and second eigenvectors per subject for cerebral artery stenosis patients.

Referring to FIG. 7A and FIG. 7B, with reference to "0" on the horizontal axis, first eigenvectors of normal persons generally have values of less than zero, and first eigenvectors of patients generally have values of greater than zero. In addition, in case of patients, the number of first eigenvectors which are larger than the value of "0" in the distribution charge of FIG. 7A is larger than that of FIG. 7B. That is, the case of using the maximum amplitude value is higher in determination of symptoms than the case of using the minimum amplitude value.

Figure 8A:
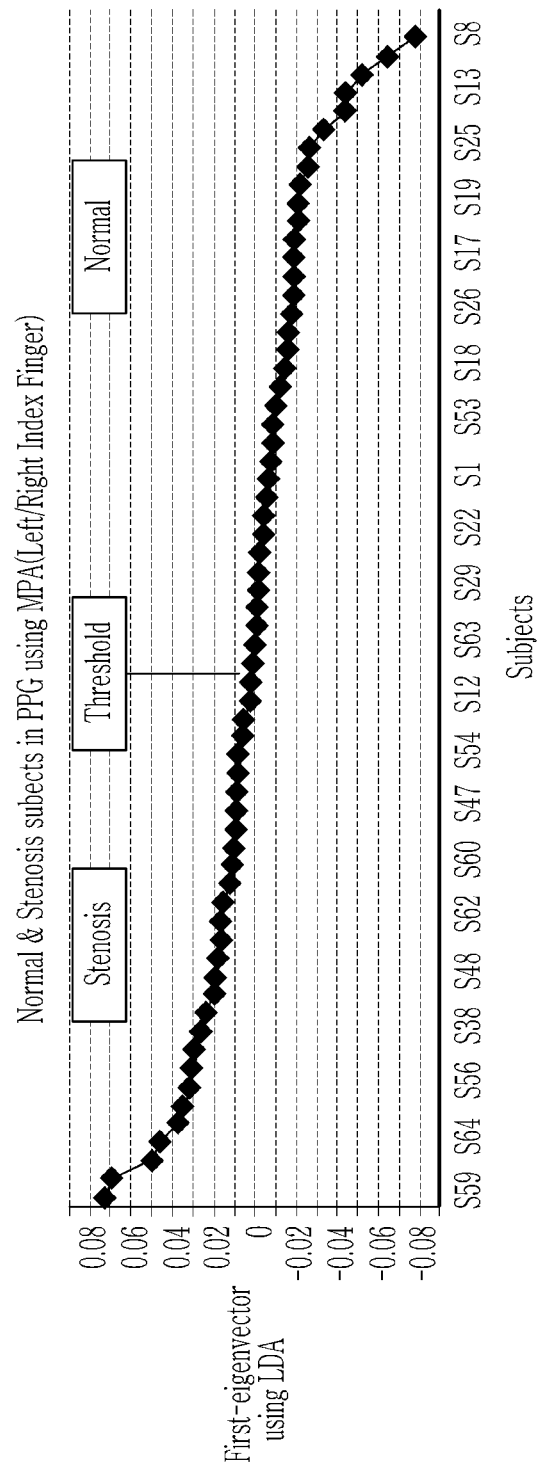
FIG. 8A and FIG. 8B are graphs that show only first eigenvectors corresponding to an amplitude value of a pulse wave signal according to the exemplary embodiment of the present invention.
Figure 8B:
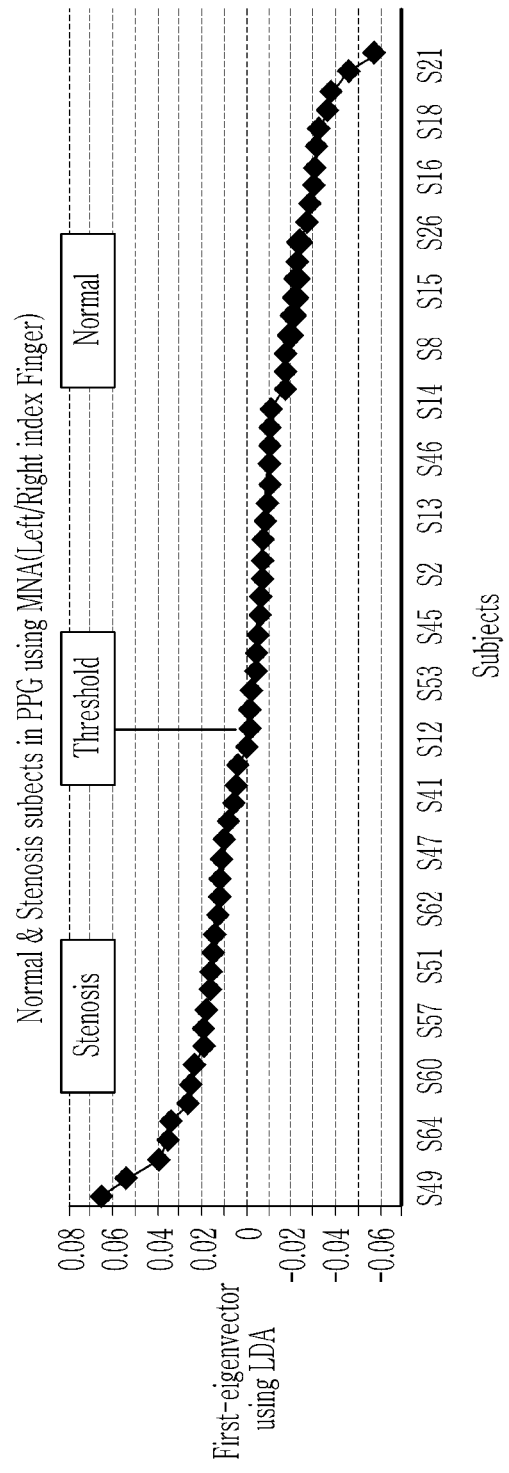

As another example, a diagnosis method in the cerebral artery stenosis diagnosis portion 190 will be described with reference to FIG. 8A and FIG. 8B. FIG. 8A and FIG. 8B are graphs that show only first eigenvectors corresponding to an amplitude value of a pulse wave signal according to the exemplary embodiment of the present invention, and the graphs shown in FIG. 8A and FIG. 8B may be displayed on the screen through the displaying portion 200.

Referring to FIG. 8A and FIG. 8B, a graph for a first eigenvector per subject is a result obtained by dividing the pulse wave signal extracted after the optimal sampling of the pulse wave signal from the index finger of each of the left and right hands into 60 feature window segments, and applying a linear determination algorithm by using a maximum amplitude value and a minimum amplitude value detected from each feature window segment to classify normal subjects and cerebral artery stenosis patients. Here, a total of 64 subjects were targeted, and 32 among the 64 were normal persons (average age: 59.8, standard deviation: 14.6), and 32 were patients (average age: 62.7, standard deviation: 11.2).

FIG. 8A is a distribution chart of first eigenvectors corresponding to a maximum positive amplitude (MPA) per subject, and FIG. 8B is a distribution chart of first eigenvectors corresponding to a maximum negative amplitude (MNA) per subject. In FIG. 8A and FIG. 8B, the horizontal axis denotes subjects, and the vertical axis denotes first eigenvectors.

Referring to FIG. 8A and FIG. 8B, it can be observed that when the first eigenvector is greater than "0", the corresponding subject is determined to be a patient, and when the first eigenvector is less than "0", the corresponding subject is determined to be a normal person, and since a range of a first eigenvector is wider in the case of using the maximum amplitude value than the case of using the minimum amplitude value, a much more precise and accurate analysis result can be acquired.

For reference, a recognition rate obtained through actual experimental results was as follows. In the experiment, pulse wave signals of the right and left fingers of the subject were extracted and used. When the maximum amplitude value was used in the pulse wave signal of the right and left fingers, the correct recognition rate was about 92.2% (59/64), when the minimum amplitude value was used in the pulse wave signal of the right and left fingers, the correct recognition rate was about 90.6% (58/64), and when the minimum and maximum amplitude values were used in the pulse wave signals of the right and left fingers, the correct recognition rate was about 90.6% (58/64).

In the correct recognition rate, "64", which is the denominator value, means a subject of the experiment, and the subjects of the experiment were 32 normal persons and 32 patients. In addition, "59" and 58", which are numerical values of the correct recognition rate, mean the number of subjects diagnosed (classified) as patients or normal persons.

Meanwhile, in the case of using the pulse wave signal of the right and left fingers, the analysis device 100 according to the exemplary embodiment of the present invention includes two PPG probes 110, and combines a right-hand pulse wave signal and a left-hand pulse wave signal that are extracted from a light signal of transmitted light or reflected light, detected by each PPG probe 110 and then uses the same.

Meanwhile, in the case of using the pulse wave signal of the right and left fingers, the analysis device 100 according to the exemplary embodiment of the present invention receives a transmitted light signal or a reflected light signal from a plurality of PPG probes 110 seated on the respective fingers, and the analysis device 100 can perform normalization using the signal obtained by combining the right-hand pulse-wave signal and the left-hand pulse-wave signal extracted from the transmitted light signal or reflected light signal, received from the PPG probes 110, and extract a first eigenvector.

In this case, the combination refers to combination of the left-hand pulse wave signal to the end of the right-hand pulse wave signal, or combination of the right-hand pulse wave signal to the end of the left-hand pulse wave signal.

The cerebral artery stenosis diagnosis portion 190 diagnoses using at least one of a pulse wave notch position per window and a wax/wane pattern per window, detected by the wax/wane wave detection portion 170 (S511). In this case, use of the pulse wave notch position per window and the wax/wane pattern per window may be set as a default, or may be used when the subject is determined to be a normal person from the diagnosis at the step S509 (S510). FIG. 5 exemplarily illustrates a case that the subject is determined to be a normal person from the diagnosis at the step S509.

The cerebral artery stenosis diagnosis portion 190 receives a pulse wave notch position for each window, determines the number of windows having the pulse wave notch position (or the number of windows that do not have the pulse wave notch position) by determining whether or not the pulse wave notch position is located for each window, determines whether the number of windows having a pulse wave notch position (or the number of windows having no pulse wave notch position) is greater than or equal to a predetermined number after determining the number of windows whose pulse wave notch position is higher than "0", and determines whether the corresponding subject is a normal person or a patient by comparing the number of windows whose pulse wave notch position is higher than a threshold value, which is "0", with the predetermined number. DeletedTexts When the number of windows having a pulse wave notch position is less than or equal to a first predetermined number or the number of windows having no pulse wave notch position is equal to or greater than a second predetermined number and the number of windows of which a pulse wave notch position is higher than the threshold, which is "0", is greater than a third predetermined number, the cerebral artery stenosis diagnosis portion 190 diagnoses the corresponding subject as a patient. For the wax/wane pattern, the cerebral artery stenosis diagnosis portion 190 measures the amount of variation in the maximum amplitude value and the minimum amplitude value over time and the amount of change in an interval between neighboring waveforms (pulse signals) in the window wax/wane pattern, and compares the amount of variation and the amount of change with a threshold to diagnose the corresponding subject as a patient if the amount of variation and the amount of change are greater than the threshold.

Figure 9B:
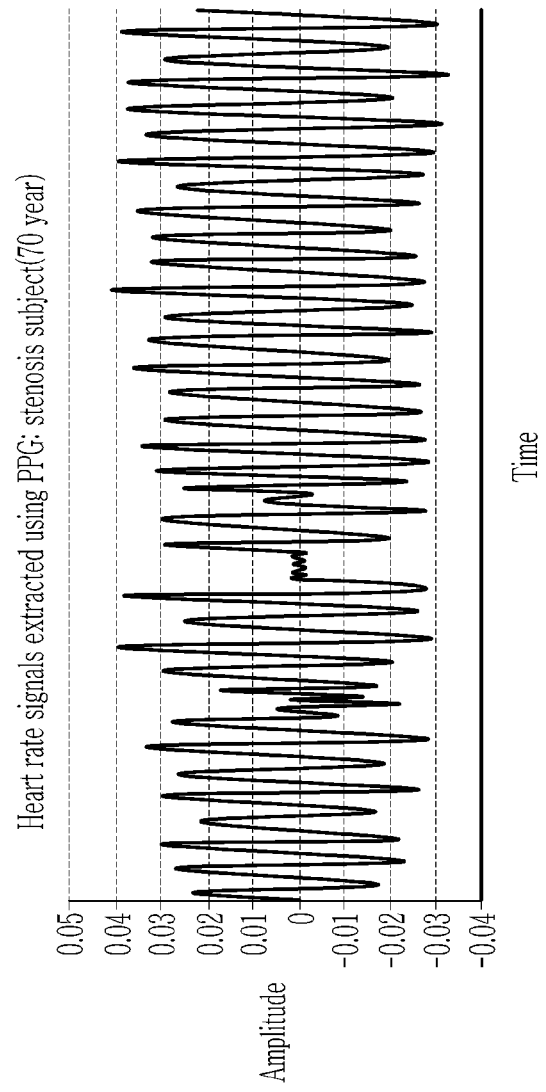

For better understanding, referring to FIG. 9A and FIG. 9B, the diagnosis using the wax/wane pattern will be described. FIG. 9A and FIG. 9B show wax/wane waveforms of a normal person and a patient according to the exemplary embodiment of the present invention.

FIG. 9A is a waveform of a normal person, and FIG. 9B is a wax/wane waveform of a patient. As shown in FIG. 9A, a wax/wane waveform of a normal person shows a large variation in the interval between neighboring waveforms (pulse signals), and the maximum and minimum amplitude values do not vary much with time. On the contrary, as shown in FIG. 9B, the wax/wane waveform of the patient shows a large variation in the interval between neighboring waveforms (pulse signals), and the variation of the maximum and minimum amplitude values with time is also large. The displaying portion 200 displays a result of a diagnosis of the cerebral artery stenosis diagnosis portion 190, the distribution of the first eigenvector shown in FIG. 7A, FIG. 7B, FIG. 8A, and FIG. 8B, and the wax/wane waveform shown in FIG. 9A and FIG. 9B on the screen (S512).

While this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

INDUSTRIAL APPLICABILITY

The device for analyzing a cerebrovascular disease and stenosis using photoplethysmography according to the exemplary embodiment of the present invention, and the method thereof, can be used in a device that diagnoses and analyzes cerebral artery stenosis and encephalopathy.

The invention claimed is:

1. A device for analyzing a cerebrovascular disease and a stenosis using photoplethysmography (PPG), comprising:
   a PPG probe configured for a finger of a subject to be seated to irradiate light to and receive light from the finger of the subject;
   a pulse wave signal extracting portion that extracts pulse wave signals from optical signals received from the PPG probe;
   a sampling portion that carries out sampling on the pulse wave signals according to a predetermined sampling condition and generates optimized pulse wave signals;
   a pulse wave signal normalization portion that generates a normalized pulse wave signal with the optimized pulse wave signals of the subject, that is optimized by the sampling portion;
   a pulse wave amplitude detection portion that divides the normalized pulse wave signal into a plurality of window segments, and detects at least one of a maximum pulse wave amplitude value or a minimum pulse wave amplitude value for each of the plurality of the window segments in the normalized pulse wave signal;
   a cerebral artery stenosis characteristic analyzing portion that extracts a first eigenvector of the subject, corresponding to pulse wave amplitude values of the plurality of window segments by applying a linear discriminant analysis to the at least one of the maximum pulse wave amplitude value or the minimum pulse wave amplitude value detected by the pulse wave amplitude detection portion for each of the window segments; and
   a cerebral artery stenosis diagnosis portion configured to compare the first eigenvector of the subject with a threshold to diagnose a characteristic of the subject,
   wherein the cerebral artery stenosis characteristic analyzing portion calculates eigenvalues corresponding to the plurality of window segments by applying the linear discriminant analysis to the at least one of the maximum pulse wave amplitude value or the minimum pulse wave amplitude value for each of the window segments, detected by the pulse wave amplitude detection portion, and determines an eigenvector having a highest eigenvalue among the calculated eigenvalues as the first eigenvector.

2. The device for analyzing the cerebrovascular disease and the stenosis using PPG of claim 1, wherein the cerebral artery stenosis characteristic analyzing portion is configured to diagnose the subject as a patient when the first eigenvector is greater than the threshold.

3. The device for analyzing the cerebrovascular disease and the stenosis using PPG of claim 2, further comprising a pulse wave notch detection portion that detects a notch position in each of the window segments, and provides notch position information,
   wherein the cerebral artery stenosis diagnosis portion is configured to diagnose the characteristic of the subject by using the notch position information.

4. The device for analyzing the cerebrovascular disease and the stenosis using PPG of claim 3, further comprising a wax/wane wave detection portion that detects a wax/wane waveform from each of the window segments,
   wherein the cerebral artery stenosis diagnosis portion is configured to diagnose the characteristic of the subject by using the wax/wane waveform.

5. The device for analyzing the cerebrovascular disease and the stenosis using PPG of claim 1, further comprising a wax/wane wave detection portion that detects a wax/wane waveform from each of the window segments,
   wherein the cerebral artery stenosis diagnosis portion is configured to diagnose the characteristic of the subject by using the wax/wane waveform.

6. A method for analyzing a cerebrovascular disease and a stenosis using photoplethysmography (PPG), comprising:
   irradiating light to and receiving light from a finger of a subject;
   extracting pulse wave signals from received optical signals;
   generating an optimized pulse wave signals by carrying out sampling on the pulse wave signals according to a predetermined sampling condition;
   generating a normalized pulse wave signal with the optimized pulse wave signals;
   dividing the normalized pulse wave signal into a plurality of window segments and detecting at least one of a maximum pulse wave amplitude value or a minimum pulse wave amplitude value for each of the window segments;
   extracting a first eigenvector of the subject, corresponding to a pulse wave amplitude value of the plurality of window segments by applying a linear discriminant analysis the at least one of the maximum pulse wave amplitude value or the minimum pulse wave amplitude value for each of the plurality of the window segments; and
   diagnosing a characteristic of the subject by comparing the first eigenvector of the subject with a threshold,
   wherein the extracting the first eigenvector includes calculating eigenvalues corresponding to the plurality of window segments by applying the linear discriminant analysis to the at least one of the maximum pulse wave amplitude value or the minimum pulse wave amplitude value for each of the window segments, and determining an eigenvector having a highest eigenvalue among the calculated eigenvalues as the first eigenvector.

7. The method for analyzing the cerebrovascular disease and stenosis using PPG of claim 6, wherein, in the diagnosing the characteristic of the subject, the subject is diagnosed as a patient when the first eigenvector is greater than the threshold.

8. The method for analyzing the cerebrovascular disease and stenosis using PPG of claim 6, further comprising:
   detecting a notch position in each of the window segments; and
   diagnosing the characteristic of the subject by using the notch position for each of the window segments.

9. The method for analyzing the cerebrovascular disease and stenosis using PPG of claim 8, further comprising:
   detecting a wax/wane waveform from each of the window segments; and
   diagnosing the characteristic of the by using the wax/wane waveform.

10. The method for analyzing the cerebrovascular disease and stenosis using PPG of claim 6, further comprising:
    detecting a wax/wane waveform from each of the window segments; and
    diagnosing the characteristic of the by using the wax/wane waveform.

11. The method for analyzing the cerebrovascular disease and stenosis using PPG of claim 6, wherein, in the extracting the pulse wave signal, a pulse wave signal of a right hand finger, a pulse wave signal of a left hand finger, or the pulse wave signal of the right hand ringer and the pulse wave signal of the left hand finger, are extracted.

* * * * *